(12) United States Patent
Meskens (10) Patent No.: US 11,878,177 B2
(45) Date of Patent: Jan. 23, 2024

(54) IMPLANTABLE MEDICAL DEVICE SHORT-RANGE RADIO SYNCHRONIZATION

(71) Applicant: Cochlear Limited, Macquarie University (AU)

(72) Inventor: Werner Meskens, Opwijk (BE)

(73) Assignee: Cochlear Limited, Macquarie University (AU)

( * ) Notice: Subject to any disclaimer, the term of this patent is extended or adjusted under 35 U.S.C. 154(b) by 271 days.

(21) Appl. No.: 17/261,716

(22) PCT Filed: Oct. 3, 2019

(86) PCT No.: PCT/IB2019/058437
§ 371 (c)(1),
(2) Date: Jan. 20, 2021

(87) PCT Pub. No.: WO2020/075021
PCT Pub. Date: Apr. 16, 2020

(65) Prior Publication Data
US 2021/0260383 A1     Aug. 26, 2021

Related U.S. Application Data

(60) Provisional application No. 62/743,673, filed on Oct. 10, 2018.

(51) Int. Cl.
*A61N 1/372* (2006.01)
*H04L 7/033* (2006.01)
*A61N 1/36* (2006.01)

(52) U.S. Cl.
CPC ....... *A61N 1/3727* (2013.01); *A61N 1/37229* (2013.01); *H04L 7/033* (2013.01); *A61N 1/36038* (2017.08)

(58) Field of Classification Search
CPC .............. A61N 1/3727; A61N 1/37229; A61N 1/36038; A61N 1/37252; H04L 7/033
See application file for complete search history.

(56) References Cited

U.S. PATENT DOCUMENTS 7,292,698 B2   11/2007   Niederdränk et al.
7,577,268 B2   8/2009    Fischer
(Continued)

FOREIGN PATENT DOCUMENTS

CN   103262435 A   8/2013
CN   103391743 A   11/2013
(Continued)

OTHER PUBLICATIONS

Search Report and the Written Opinion in corresponding International Application No. PCT/IB2019/058437, dated Jan. 23, 2020, 9 pages.
(Continued)

*Primary Examiner* — Tammie K Marlen
(74) *Attorney, Agent, or Firm* — Edell, Shapiro & Finnan, LLC (57) ABSTRACT

Presented herein are techniques for generating a stable reference clock for use by a short-range radio transceiver of an implantable component without the need for an X-tal oscillator within the implantable component itself. In accordance with certain techniques presented herein, the implantable component is in communication with a first external component via a closely-coupled link and in communication with a second external component via short-range radio link. The implantable component is configured to receive, from the first external component, signals via the closely-coupled link. The implantable component is configured to extract frequency information from these received signals and syn-
(Continued)

chronize a carrier frequency of the short-range radio link to the frequency information extracted from the signals.

20 Claims, 6 Drawing Sheets

(56) References Cited

U.S. PATENT DOCUMENTS

| | | |
|---|---|---|
| 7,831,056 B2 | 11/2010 | Nikles et al. |
| 9,247,354 B2 | 1/2016 | Boguslavskij et al. |
| 2001/0056291 A1 | 12/2001 | Zilberman et al. |
| 2005/0131494 A1 | 6/2005 | Park et al. |
| 2012/0109256 A1 | 5/2012 | Meskins et al. |
| 2012/0232616 A1 | 9/2012 | Van Baelen et al. |
| 2013/0138991 A1 | 5/2013 | Reinke et al. |
| 2018/0279060 A1 | 9/2018 | Bodvarsson |

FOREIGN PATENT DOCUMENTS

| | | |
|---|---|---|
| CN | 107921267 A | 4/2018 |
| KR | 10-2014-0092238 A | 7/2014 |

OTHER PUBLICATIONS

Uo, H., et a;., "A digital crystal-less clock generation scheme for wireless biomedical implants," 2016 IEEE Biomedical Circuits and Systems Conference (BioCAS), Shanghai, 2016, pp. 480-483, doi: 10.1109/BioCAS.2016.783383; Source: http://ieeexplore.ieee.org/document/7833836/.

Crystal-less clock generators—DSC2311—Micrel. Datasheet—Jan. 2016 (18 sheets).

IMPLANTABLE MEDICAL DEVICE SHORT-RANGE RADIO SYNCHRONIZATION

BACKGROUND

Field of the Invention

The present invention generally relates to implantable medical devices.

Related Art

Systems having one or more components implanted in a recipient, generally referred to herein as implantable medical device systems, have provided a wide range of therapeutic benefits to recipients over recent decades. In particular, partially or fully-implantable medical device systems such as hearing prosthesis systems (e.g., systems that include bone conduction devices, mechanical stimulators, cochlear implants, etc.), implantable pacemakers, defibrillator systems, functional electrical stimulation device systems, etc., have been successful in performing lifesaving and/or lifestyle enhancement functions for a number of years.

The types of implantable medical device systems and the ranges of functions performed thereby have increased over the years. For example, many implantable medical device systems now often include one or more instruments, apparatus, sensors, processors, controllers or other functional mechanical or electrical components that are permanently or temporarily implanted in a recipient. These functional implantable components are typically used to diagnose, prevent, monitor, treat, or manage a disease/injury or symptom thereof, or to investigate, replace or modify the anatomy or a physiological process. Many of these functional implantable components utilize power and/or data received from external devices that are part of, or operate in conjunction with, the implantable medical device system.

SUMMARY

In one aspect, a method performed at an implantable component in communication with a first external component via a closely-coupled link and in communication with a second external component via short-range radio link is provided. The method comprises: receiving, from the first external component, closely-coupled signals via the closely-coupled link; extracting frequency information from the received closely-coupled signals; and synchronizing a carrier frequency of the short-range radio link to the frequency information extracted from the closely-coupled signals.

In another aspect an implantable component of an implantable medical device system is provided. The implantable component comprises: a first receiver configured to receive signals via a first communication link; a short-range radio transceiver configured to receive data via a short-range radio link, wherein the short-range radio transceiver is configured to operate at a pre-determined carrier frequency; and a reference clock extractor configured to generate, based on frequency information extracted from the signals received via the first communication link, a reference clock for use by the short-range radio transceiver in communication via the short-range radio link.

In another aspect an implantable component of an implantable medical device system is provided. The implantable component comprises: a first implantable coil coupled to a first external component via a closely-coupled link and configured to receive closely-coupled signals; a reference clock extractor circuit configured to extract frequency information from the closely-coupled signals received via the first implantable coil and to generate a reference clock based on the frequency information extracted from the closely-coupled signals; and a short-range radio transceiver configured to use the reference clock to at least one of transmit data signals to, or receive data signals from, a second external device via a short-range radio link.

BRIEF DESCRIPTION OF THE DRAWINGS

Embodiments of the present invention are described herein in conjunction with the accompanying drawings, in which.

DETAILED DESCRIPTION

Future implantable medical device systems may include implantable components that make use of a short-range radio link, such as a magnetic induction (MI) link, for wireless transfer of data to/from the implantable component. Such implantable medical components will include a short-range radio transceiver (e.g., MI-radio) for transferring the data using modulation schemes such as, for example, frequency-shift keying (FSK), bi-phase-shift keying (BPSK), quadrature-phase-shift keying (QPSK), offset QPSK (OQPSK), minimum-shift keying (MSK), on-off keying (OOK), etc. As such, the frequency/frequencies of the short-range radio transceiver, including those used by the transmitter blocks and the receiver blocks, need to be derived according to a stable clock reference. That is, radio receiver and transmitter blocks both require precise frequency references for proper operation. If the clock reference used to generate these frequency reference(s) is unstable, then the transmit or receive frequency/frequencies of the transmit and receiver blocks may drift considerably and operate outside the tuning of the radio antennas of remote (external) receivers or transmitters.

One solution is include a crystal (X-tal) oscillator, such as quartz oscillator, in the implantable component. A crystal oscillator is an electronic circuit that uses the mechanical resonance of a vibrating crystal to generate a sinusoidal electronic signal at a very precise frequency. The stability of a quartz oscillator, in particular, is typically 60 parts per million (ppm) Hz, while a free running oscillator (FRO) has a stability of +/−10%. A FRO of an MI radio at 11.6 MHz would drift with +/−1,160 MHz, compared to +/−696 Hz with a quartz. Such drifts become more and more problematic over increasing periods of time.

Since X-tal oscillators inherently generate a stable clock, these types of oscillators have been used successfully in a variety of transceivers. However, there is a drive to make implantable components as small as possible and X-tal oscillators require a considerable amount of space to implement (e.g., the crystal itself consumes physical space that inherently increases the size of the device). With future implantable components, there may be little or no room to implement this type of crystal element inside the component and/or this type of element may cause a degraded device reliability.

Accordingly, presented herein are techniques for generating a stable reference clock for use by a short-range radio transceiver of an implantable component without the need for an X-tal oscillator within the implantable component itself. In accordance with certain techniques presented herein, the implantable component is in communication with a first external component via a closely-coupled link and in communication with a second external component via short-range radio link. The implantable component is configured to receive, from the first external component, signals via the closely-coupled link. The implantable component is configured to extract frequency information from these received signals and synchronize a carrier frequency of the short-range radio link to the frequency information extracted from the signals.

More particular, the implantable component derives a reference clock for use by a short-range radio transceiver from the frequency information extracted from the signals received via the closely-coupled link. The implantable component then generates, with one or more implantable frequency sources in the implantable component, one or more frequency signals based on the reference clock, and uses the one or more frequency signals to at least one of transmit or receive data signals via the short-range radio link. As such, the techniques presented herein address the need for hardware/components inside the implantable component to generate an accurate or stable clock reference (e.g., avoid the need for an X-tal oscillator, SAW/BAW, ceramic resonators, etc.) for an MI radio or other short range radio transceivers. This facilitates the construction of smaller implantable components and increases reliability (e.g., by avoiding an X-tal oscillator which must be stressed first to discover any presence of micro-cracks.

There are a number of different types of implantable medical device systems in which embodiments presented herein may be implemented. However, merely for ease of illustration, the techniques presented herein are primarily described with reference to one type of implantable medical device system, namely a cochlear implant system. It is to be appreciated that the techniques presented herein may be used in any other partially or fully implantable medical device systems now known or later developed, including other auditory prosthesis systems, such as auditory brainstem stimulator systems, electro-acoustic hearing prosthesis systems, middle ear prosthesis systems, direct cochlear stimulator systems, bimodal hearing prosthesis systems, etc. and/or other types of medical devices, such as visual prosthesis systems, pain relief implant systems, pacemakers, etc.

Figure 1A:
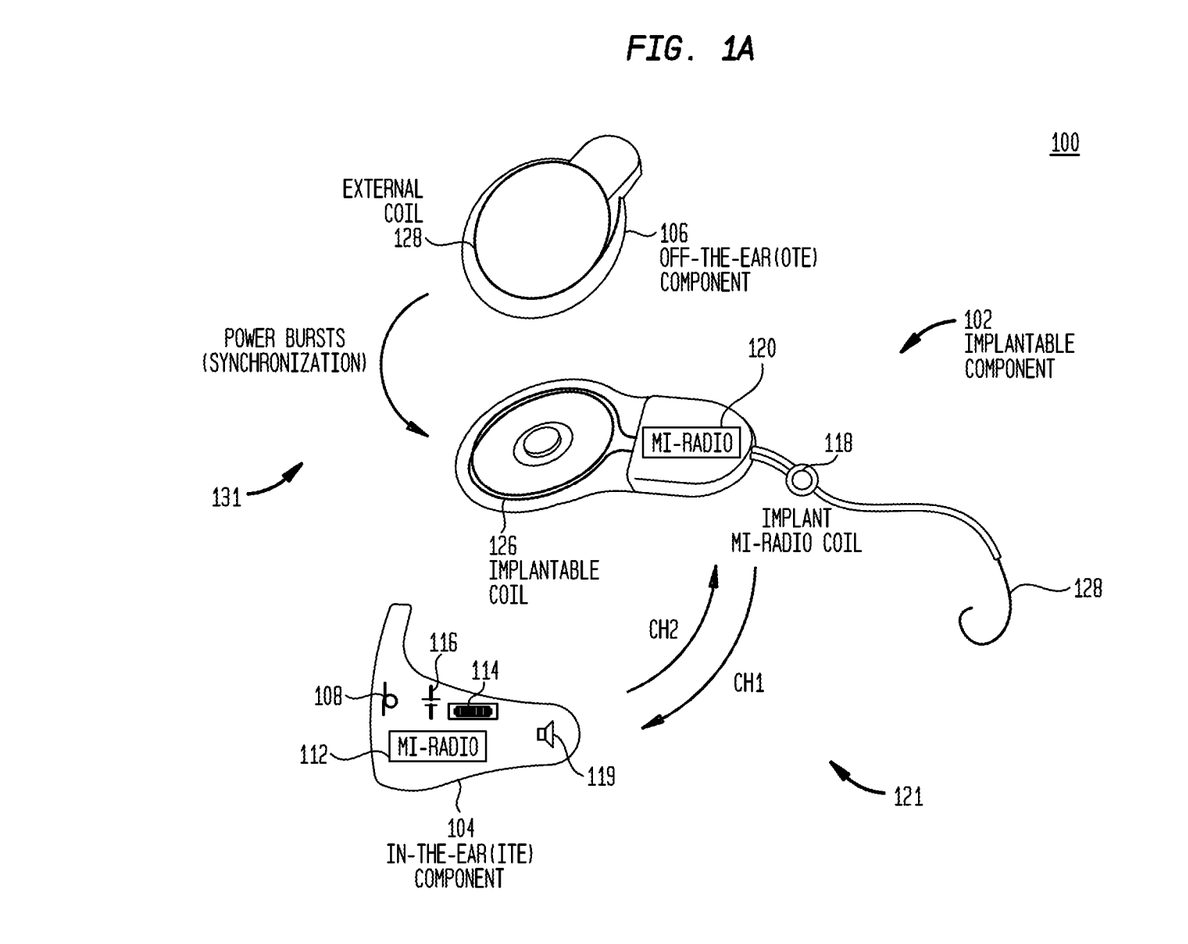
FIG. 1A is a schematic diagram illustrating an implantable medical device system, in accordance with certain embodiments presented herein.
Figure 1B:
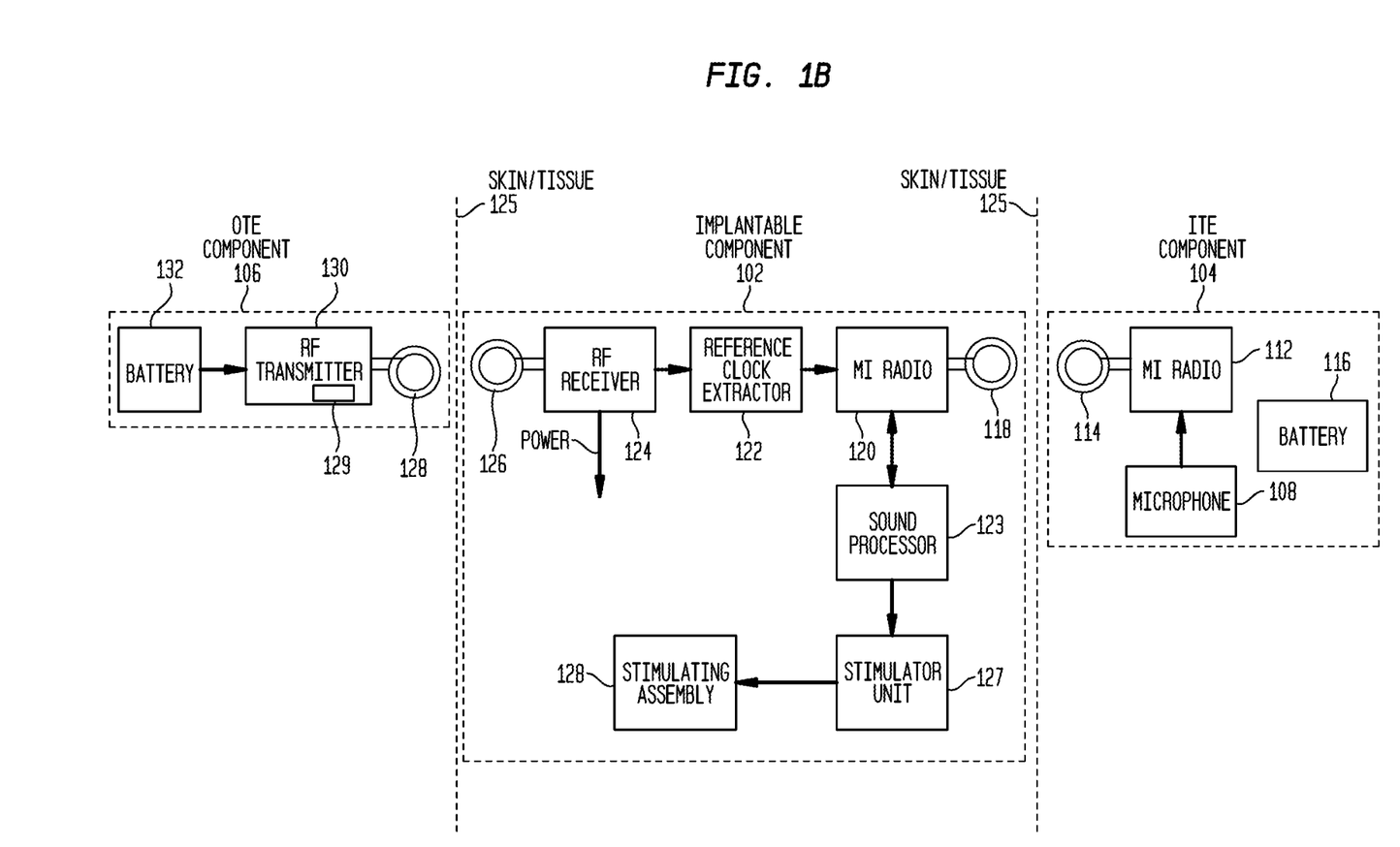
FIG. 1B is functional block diagram illustrating the implantable medical device system of FIG. 1A, in accordance with certain embodiments presented herein.

FIG. 1A is schematic diagram of an exemplary cochlear implant system 100 configured to implement the techniques presented herein, while FIG. 1B is a block diagram of the cochlear implant system 100. For ease of description, FIGS. 1A and 1B will be described together.

The cochlear implant system 100 comprises an implantable component 102, a first external component 104, and a second external component 106. In this example, the first external component 104 is configured to be worn in the ear canal of a recipient. As such, the specific external component 104 of FIGS. 1A and 1B is sometimes referred as an in-the-ear (ITE) component 104. The second external component 106 is an external charging device (external charger) in the shape of a button configured to be worn "off-the-ear" of a recipient. As such, the specific external charger 106 of FIGS. 1A and 1B is also sometimes referred to as an off-the-ear (OTE) component or button.

The ITE component 104 comprises one or more sound input devices configured to receive/capture sound signals. FIGS. 1A and 1B illustrate one example sound input device, namely a microphone 108. However, it is to be appreciated that additional microphones and additional types of sound input devices (e.g., telecoils, etc.) may also be included in the ITE component 104. The ITE component 104 also includes a short-range radio transceiver, which in this example is a magnetic induction (MI) radio 112, as well as an MI coil 114, a speaker 119, and a battery 116. The battery 116 is configured to provide power for the various components of the ITE sound processing unit 104. However, merely for ease of illustration, connections between the battery 104 and the other components have been omitted from FIGS. 1A and 1B.

As noted, the microphone 108 (and/or any other sound input devices) is configured to receive/capture sound signals. If not already in electric form, the sound signals are converted to electrical signals. In the embodiment of FIGS. 1A and 1B, these electrical signals, referred to herein as sound or audio data, are provided to the MI radio 112, which transfers the sound data signals (e.g., in an encoded manner) to the implantable component 102 via the MI coil 114.

The implantable component 102 comprises a short-range radio transceiver, which in this example is an MI radio 120, connected to an MI coil 118. As shown in FIG. 1B, the MI radios 112, 120 use the MI coils 114, 118 to form a bi-directional short-range radio link 121 for transfer of data between the implantable component 102 and the ITE component 104. In certain examples, the short-range radio link 121 is referred to as having two channels, where one channel is used to send data from the ITE component 104 to the implantable component 102, and one channel is used to send data from the implantable component 102 to the ITE component (i.e., 1 channel in each direction). As shown in FIG. 1B, the short-range radio link 121 is a transcutaneous link that transfers the data through the skin/tissue 125 of the recipient.

The MI radio 120 is configured to provide received sound data to a sound processor 123. The sound processor 123 is configured to convert sound signals into stimulation control signals for use in stimulating a first ear of a recipient. Stated differently, the sound processor 123 (e.g., one or more processing elements implemented as firmware, software, etc.) is configured to convert the sound signals received at the ITE component 104 into stimulation control signals that represent electrical stimulation for delivery to the recipient.

The stimulation control signals are provided to stimulator unit 127 for use in delivering electrical stimulation (current) to a cochlea of the recipient via a stimulating assembly 128. That is, the stimulating assembly 128 is configured to be at least partially implanted in the recipient's cochlea (not shown) and includes a plurality of longitudinally spaced intra-cochlear electrical stimulating contacts (electrodes) that deliver electrical stimulation (current) to the recipient's cochlea. In this way, cochlear implant system 100 electrically stimulates the recipient's auditory nerve cells, bypassing absent or defective hair cells that normally transduce acoustic vibrations into neural activity, in a manner that causes the recipient to perceive one or more components of the input audio signals.

In order to stimulate the recipient's cochlea, the implantable component 102 requires electrical power for continued operation. In the embodiments of FIGS. 1A and 1B, this operating power is provided by the OTE component 106. More specifically, the implantable component 102 comprises a radio frequency (RF) receiver 124 and an implantable RF coil 126. Implantable RF coil 126 is typically a wire antenna coil comprised of multiple turns of electrically insulated single-strand or multi-strand platinum or gold wire. The RF receiver 124 may consist of a cascade of tuned amplifiers The OTE component 106 also includes an external wire antenna coil (external coil) 128 comprised of multiple turns of electrically insulated copper wire. The OTE component 106 further comprises an RF transmitter 130 and a battery 132. Generally, a magnet (not shown in FIGS. 1A and 1B) is fixed relative to each of the implantable coil 126 and the external coil 128. These magnets facilitate the operational alignment of the external coil 128 with the implantable coil 126, which in turn enables the OTE component 106 to transmit power, as well as possibly data, to the implantable component 102 via a closely-coupled wireless link 131 formed between the external coil 128 and the implantable coil 126. Stated differently, the transmitter 130 transcutaneously transfers (e.g., through skin/tissue 125 of the recipient) power from the battery 132 to the implantable component 102 via the coils 128 and 126. In the examples of FIGS. 1A and 1B, the closely-coupled wireless link 131 is a radio frequency (RF) link. However, various other types of energy transfer, such as infrared (IR), electromagnetic, capacitive and inductive transfer, may be used to transfer the power and/or data from the external component to the implantable component. Although not shown in FIG. 1B, the power received at the RF receiver 124 (from the OTE component 106) may be distributed to the other components of the implantable component 102 for operation thereof.

It is to be appreciated that the specific use of an ITE component 104 and an OTE component 106, as shown in FIGS. 1A and 1B, is merely illustrative and that the techniques presented herein may be implemented with other types of external components. For example, in an alternative arrangement, the OTE component 106 could be replaced by a behind-the-ear component that is attached to a separate coil via a cable. Other variations, such as a headpiece coil wired to a battery pack, a charging headband, etc. are also possible.

In summary, FIGS. 1A and 1B illustrate an arrangement in which implantable component 102 receives power, and possibly data, from a first external component (i.e., OTE component 106), and in which the implantable component 102 receives data, and possibly sends data to, a second external component (i.e., ITE component 104). The implantable component 102 receives the power from the OTE component 106 via a closely-coupled link 131, while the implantable component 102 receives the data from the ITE component 104 via an MI link 121.

MI communication is useful for transferring data (e.g., audio or stimulation data streams) between the ITE component 104 and the implantable component 102 because, for example, MI device communication is based on a single frequency channel and may use larger bandwidths by radio regulatory grant compared to other more common short range communication mechanisms. However, one issue with MI communication is that the MI radios 112 and 120 each need a stable clock source for use in deriving the carrier frequency of the MI link. As noted above, if the clock source used to generate the carrier frequency/frequencies used by a radio is unstable, then the transmit or receive frequency/frequencies may drift considerably and operate outside the tuning of the opposing receiver/transmitter.

For external components, such as ITE component 104, the typical solution is use a crystal (X-tal) oscillator as the stable clock source. However, the use of an X-tal oscillator in an implantable component, such as implantable component 102, may be problematic or difficult (e.g., decreased reliability and/or there may be little or no room to for the crystal within the implantable component). As such, presented herein are techniques that enable the implantable component 102 to generate a stable reference clock for the MI radio 120 without the need for an X-tal oscillator within the implantable component 102 itself.

More specifically, as described further below, the implantable component 102 receives signals via the closely-coupled link 131 with OTE component 106. The OTE component transmits signal on the closely-coupled link 131 with precise timing/frequency, which is set based on an inherently stable clock source 129. The stable clock source 129 may be, for example, an X-tal oscillator.

The implantable component 102 comprises a reference clock extractor 122 that is configured to extract frequency information from the signals received at the RF receiver 124 via closely coupled link 131. The reference clock extractor 122 uses the extracted frequency information to derive a reference clock for use by the MI radio 120 to at least one of transmit or receive signals via the magnetic induction link 121. As a result, and as described further below, the carrier frequency of the MI link 121 is synchronized or locked to the frequency information extracted from the signals received via closely coupled link 131.

Figure 2:
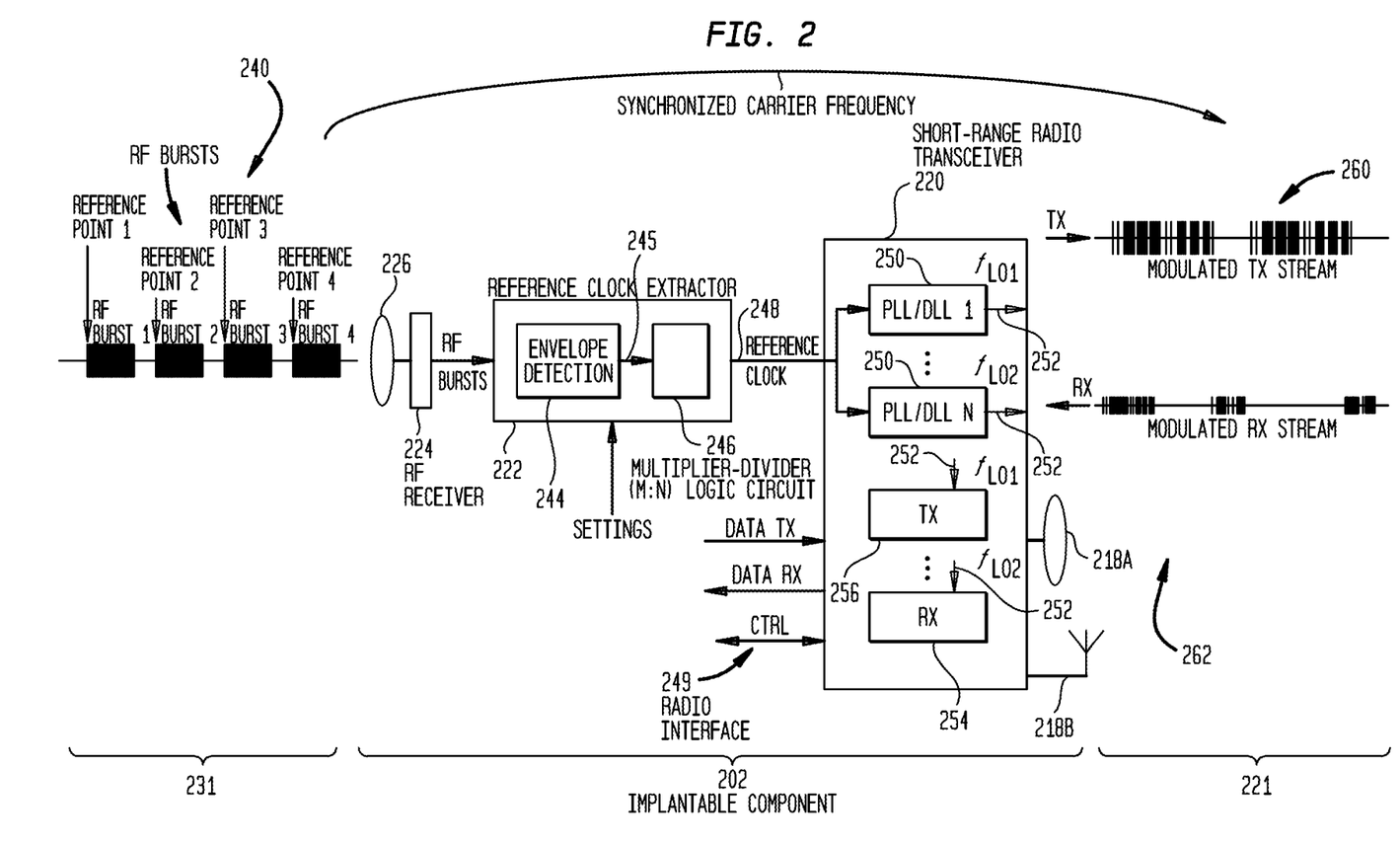
FIG. 2 is schematic block illustrating portion of an implantable component of an implantable medical device system, in accordance with certain embodiments presented herein.
Figure 3:
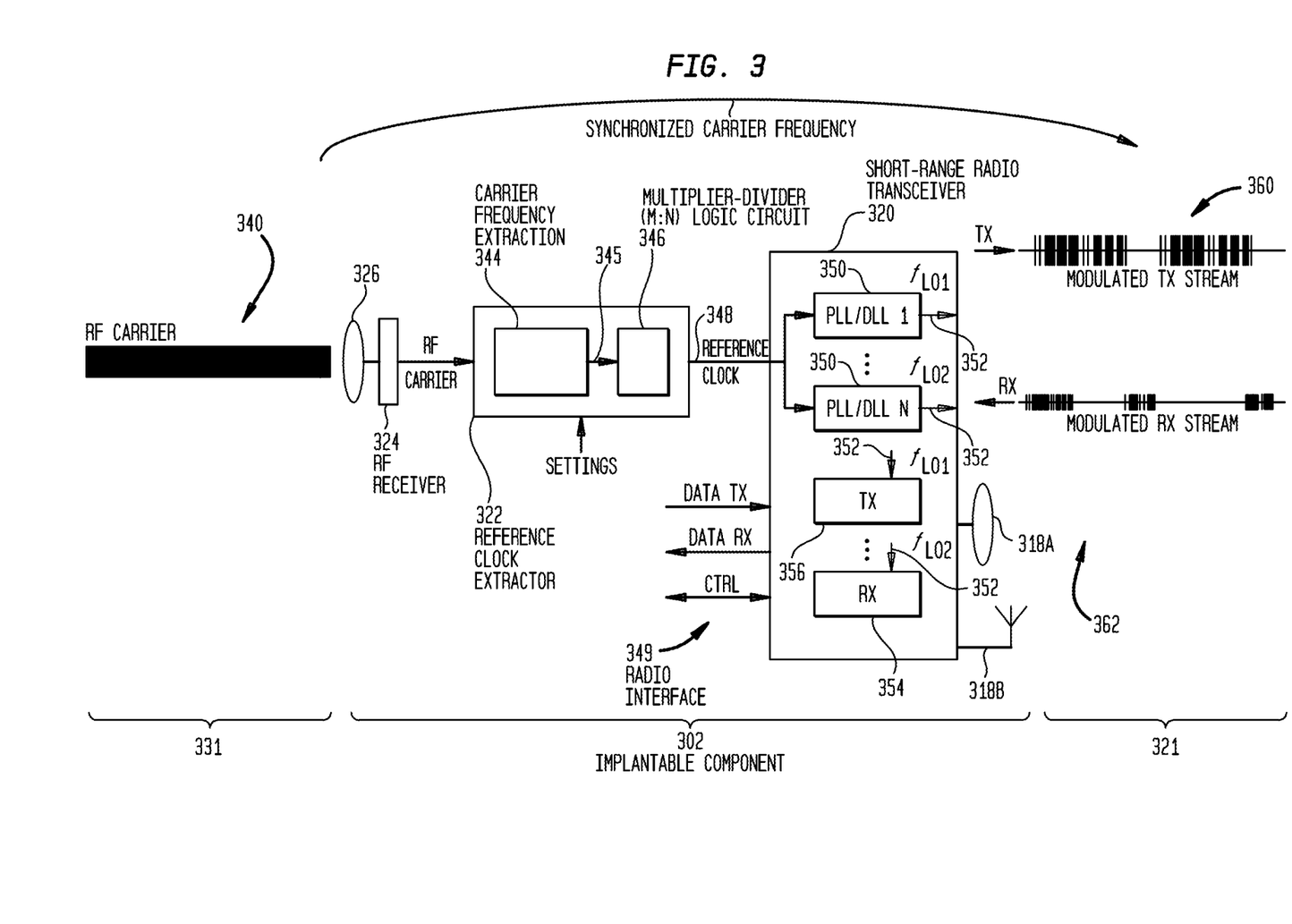
FIG. 3 is schematic block illustrating portion of an implantable component of an implantable medical device system, in accordance with certain embodiments presented herein.

As noted, FIGS. 1A and 1B have primarily been described with reference to a cochlear implant system comprising an ITE component, an OTE component, and implantable component. However, it is to be appreciated that the techniques presented herein may be used in cochlear implant systems having other arrangements, and that the techniques presented herein may be used in other types of implantable medical device systems in which an implantable component communicates with multiple separate devices/components using different/separate communication links. FIGS. 2 and 3 illustrate operation of two example implantable components of two implantable medical device systems (e.g., visual prosthesis systems, pain relief implant systems, pacemakers, cochlear implant systems or other auditory prosthesis systems, such as auditory brainstem stimulator systems, electroacoustic hearing prosthesis systems, middle ear prosthesis systems, direct cochlear stimulator systems, bimodal hearing prosthesis systems, etc.), in accordance with embodiments presented herein.

More specifically, FIG. 2 is schematic diagram illustrating further details of one arrangement of an implantable component 202 configured to synchronize a carrier frequency of a short-range radio link 221, such as a magnetic induction link, to frequency information extracted from power signals received via a separate closely coupled link 231. For ease of illustration, FIG. 2 only illustrates several elements of implantable component 202 that are relevant to the carrier frequency synchronization, namely an implantable coil 226, a reference clock extractor 222, a short range radio transceiver (e.g., magnetic induction radio) 220, and an antenna 218 (e.g., magnetic induction coil 218A or an open-ended or dipole antenna 218B). In this example, the reference clock extractor 222 and the short-range radio transceiver 220 are connected by a radio interface 249.

FIG. 2 also illustrates power signals 240 that are received from a first external device (not shown in FIG. 2) at an implantable coil 226 of the implantable component 202 over a closely-coupled link 231. The power signals 240 are a series of "RF bursts," where power is provided for a specified period of time at specified intervals (i.e., at a specified frequency). In the example of FIG. 2, the RF bursts are provided (e.g., sent) at a rate of every 50 microseconds (i.e., a frequency of 20 kilohertz (kHz)). The illustrative carrier frequency for the closely coupled link in this example is 6.78 megahertz (MHz). It is to be appreciated that the above specific carrier frequency, as well as the specific frequency of RF bursts (burst rate), are merely illustrative and that other embodiments may use different frequencies (e.g., the burst rate may be 100 us, 1 ms, etc., while the carrier frequency for the closely coupled link may be 5 MHz, 3.56 MHz, 27.12 MHz, etc.).

In this example, the first external device generates the power signals 240 with precise timing and frequency (e.g., the rate of every 50 microseconds and carrier frequency of 6.78 MHz are exact and consistent/regular). This precise timing/frequency is set based on an inherently stable clock source in the external component, such as an X-tal oscillator.

As shown, the RF bursts 240 are provided via the receiver 224 to the reference clock extractor 222. The reference clock extractor 222 includes an envelope detection circuit 244 and a multiplier-divider (M:N) logic circuit 246. The envelope detection circuit 244 includes an envelope detector, which is an electronic circuit that is configured to generate an output which is the envelope of the RF bursts 240 (e.g., a smooth curve outlining the extremes of the RF bursts). In on example, the envelope detector 244 may comprise a diode and a resistor-capacitor circuit (RC) circuit connected to the diode. The multiplier-divider (M:N) logic circuit 246 may be, for example, a combination of flip-flops, registers, and/or logic gates. In one example, a divider by N is applied to convert 5 MHz into 9.766 kHz by cascading nine (9) flip-flops, each with a division ratio of two (2) since $2^9=512$ and 5 MHz: 512=9.766 kHz or 102.4 us.

When the RF bursts 240 are received at the reference clock extractor 242, the envelope detection circuit 244 determines the envelope of the RF bursts 240, which in turn can be used by the envelope detection circuit 244 to determine the burst rate thereof. In FIG. 2, the burst rate, which is represented by arrow 245, is provided to the multiplier-divider (M:N) logic circuit 246. The stable/consistent burst rate 245 of the RF bursts (power signals) 240 received over the closely-coupled link is used to stabilize/adjust the short-range radio transceiver 220 operation frequency. As a result, the multiplier-divider (M:N) logic circuit 246 generates a stable reference clock signal (reference clock) 248 for the short-range radio transceiver 220, which frequency or phase directly relates to the burst rate 245 of the power signals received via the closely-coupled link. In certain embodiments, the multiplier-divider (M:N) logic circuit 246 may be optional, bypassed, or M:N may be set at 1:1 (i.e., when the operation frequency of the short-range radio transceiver 220 matches the burst rate 240).

The reference clock 248 (e.g., divided or/and multiplied burst rate) is the reference signal to one or more implantable frequency sources 250 of the short range radio transceiver (e.g., MI radio) 220. As such, the reference clock 248 is sometimes referred to herein as a "transceiver reference clock." The implantable frequency sources 250 of the short range radio transceiver 220 may be, for example, phase locked loops (PLLs) or delay locked loops (DLLs).

The implantable frequency sources 250 each output a frequency signal 252. These frequency signals 252 (e.g., PLL/DLL output signals) are used as a local oscillator (LO) by the receiver block(s) 254 (e.g., mixer stage of the radio receiver) and the transmitter block(s) 256 (e.g., generating the modulated carrier signal).

For example, shown in FIG. 2 is a modulated transmitter (TX) stream 260 generated by a transmitter bock 256 of the short range radio transceiver 220 for transmission via antenna 218 over a short-range radio link 221 to a second external device (not shown in FIG. 2), which is separate from the first external device. The modulated TX stream 260 includes a carrier frequency of 11.6 MHz, which is modulated with data using, for example, frequency-shift keying (FSK), bi-phase-shift keying (BPSK), quadrature-phase-shift keying (QPSK), offset QPSK (OQPSK), minimum-shift keying (MSK), on-off keying (OOK), etc. The 11.6 MHz carrier frequency is generated from a frequency signal 252 generated by an implantable frequency source 250.

Also shown in FIG. 2 is a modulated receiver (RX) stream 262 received at a receiver block 254 of the short range radio transceiver 220 via antenna 218 over the short-range radio link 221 with the second external device. The modulated RX stream 262 includes a carrier frequency of 11.6 MHz, which is modulated with data using, for example, FSK, BPSK, QPSK, OQPSK, MSK, OOK, etc. A frequency signal 252 generated by an implantable frequency source 250 is used to generate the frequency that is mixed with the incoming modulated RX stream 262 so that it can be changed in frequency to a common value for processing and recovery of the modulated data.

In summary, FIG. 2 illustrates that the carrier frequency of the of the short-range radio link 221 (e.g., the modulated TX and RX streams) is synchronized to frequency information, namely a RF burst rate 245, extracted from power signals 240 (RF bursts) provided to the implantable component 202 over the closely-coupled link 231, where the closely-coupled link 231 is separate and distinct from the short-range radio link 221. As detailed above, the implantable component 202 is configured to extract the RF burst rate 245 from the power signals 240 and to derive a reference clock 248 from this frequency information extracted from the power signals 240. The reference clock 248 is then used by the short-range radio transceiver 220 to at least one of transmit or receive signals on the short-range radio link 221.

FIG. 3 is schematic diagram illustrating further details of one arrangement of an implantable component 302 configured to synchronize a carrier frequency of a short-range radio link 321, such as a magnetic induction link, to frequency information extracted from power signals received via a separate closely coupled link 331. For ease of illustration, FIG. 3 only illustrates several elements of implantable component 302 that are relevant to the carrier frequency synchronization, namely an implantable coil 326, a reference clock extractor 322, a short range radio transceiver (e.g., magnetic induction radio) 320, and an antenna (e.g., magnetic induction coil 318A or an open-ended or dipole antenna 318B). In this example, the reference clock extractor 322 and the short-range radio transceiver 320 are connected by a radio interface 349.

FIG. 3 also illustrates a power signal 340 that is received at an implantable coil 326 of the implantable component 302 over a closely-coupled link 331. In this example, the power signals 340 is a continuous signal transmitted, for at least a period time, at a specific carrier frequency. In FIG. 3, the carrier frequency is 6.78 MHz, but it is to be appreciated that the above specific carrier frequencies merely illustrative and that other embodiments may use different frequencies (e.g., 5 MHz, etc.).

In this example, the first external device generates the power signals 340 with precise timing and at the precise carrier frequency. This precise timing/frequency is set based on an inherently stable clock source in the external component, such as an X-tal oscillator.

As shown, the power signal 340 is provided to the reference clock extractor 322 via receiver 324. The reference clock extractor 342 includes a carrier frequency extraction circuit 344 and a multiplier-divider (M:N) logic circuit 346. The multiplier-divider (M:N) logic circuit 346 may be, for example, a combination of flip-flops, registers, and/or logic gates.

Figure 4:
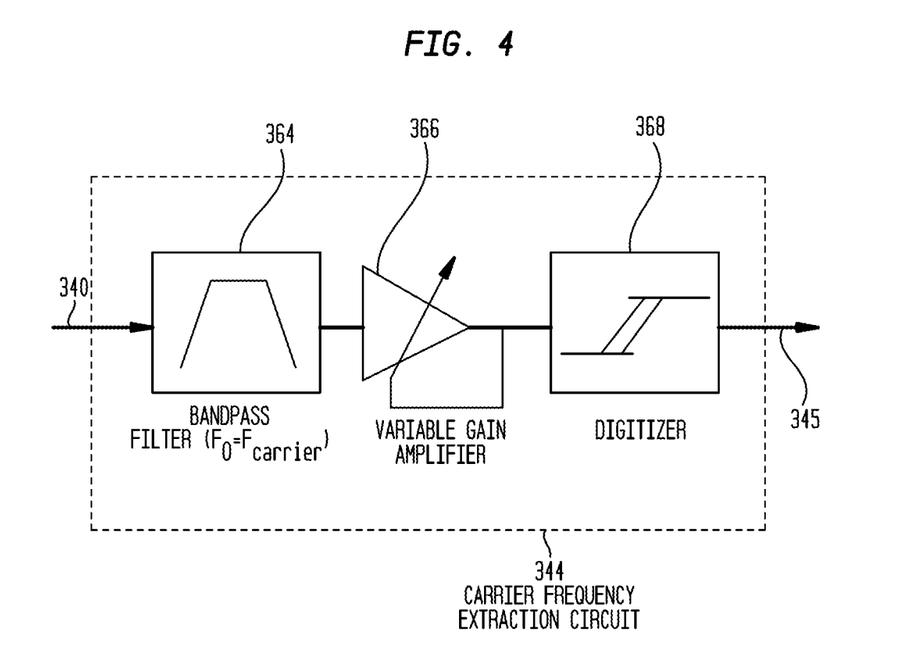
FIG. 4 is a schematic block diagram illustrating a carrier frequency extraction circuit, in accordance with certain embodiments presented herein.

As shown in FIG. 4, the carrier frequency extraction circuit 344, in this specific example, includes a bandpass filter 364, a variable gain amplifier 366, and a digitizer 368. The bandpass filter 364 has a center frequency ($f_o$) that matches the carrier frequency of the power signal 340. As such, as shown in FIG. 4, the incoming power signal 340 is filtered by the bandpass filter 364, amplified (if needed) at the variable gain amplifier 366, and digitized at digitizer 368 to derive a square wave, which is shown in FIGS. 3 and 4 by arrows 345.

In FIG. 3, the square wave 345 is provided to the multiplier-divider (M:N) logic circuit 346 and used to stabilize/adjust the short-range radio transceiver 320 operation frequency. In particular, the multiplier-divider (M:N) logic circuit 346 generates a stable reference clock signal (reference clock) 348 for the short-range radio transceiver 320, which frequency or phase directly relates to the carrier frequency of the power signals received via the closely-coupled link.

The reference clock 348 is the reference signal to one or more implantable frequency sources 350 of the short range radio transceiver (e.g., MI radio) 320. As such, the reference clock 348 is sometimes referred to herein as a "transceiver reference clock." The implantable frequency sources 350 of the short range radio transceiver 320 may be, for example, phase locked loops (PLLs) or delay locked loops (DLLs).

The implantable frequency sources 350 each output a frequency signal 352. These frequency signals 352 (e.g., PLL/DLL output signals) are (e.g., by a division ratio of 1 to N) used as a local oscillator (LO) by the receiver block(s) 354 (e.g., mixer stage of the radio receiver) and the transmitter block(s) 356 (e.g., generating the modulated carrier signal).

For example, shown in FIG. 3 is a modulated transmitter (TX) stream 360 generated by a transmitter bock 356 of the short range radio transceiver 320 for transmission via antenna 318 (e.g., coil 318A or open-ended or dipole antenna 318B) over a short-range radio link 321 to a second external device (not shown in FIG. 3). The modulated TX stream 360 includes a carrier frequency of 11.6 MHz, which is modulated with data using, for example, frequency-shift keying (FSK), bi-phase-shift keying (BPSK), quadrature-phase-shift keying (QPSK), offset QPSK (OQPSK), minimum-shift keying (MSK), on-off keying (OOK), etc. The 11.6 MHz carrier frequency is generated from a frequency signal 352 generated by an implantable frequency source 350.

Also shown in FIG. 3 is a modulated receiver (RX) stream 362 received at a receiver block 354 of the short range radio transceiver 320 via antenna 318 over the short-range radio link 321. The modulated RX stream 362 includes a carrier frequency of 11.6 MHz, which is modulated with data using, for example, FSK, BPSK, QPSK, OQPSK, MSK, OOK, etc. A frequency signal 352 generated by an implantable frequency source 350 is used to generate the frequency that is mixed with the incoming modulated RX stream 362 so that it can be changed in frequency to a common value for processing and recovery of the modulated data.

In summary, FIG. 3 illustrates that the carrier frequency of the of the short-range radio link 321 (e.g., the modulated TX and RX streams) is synchronized to frequency information, namely a carrier frequency extracted from power signals 340 provided to the implantable component 302 over the closely-coupled link 331, where the closely-coupled link 331 is separate and distinct from the short-range radio link 321. As detailed above, the implantable component 302 is configured to extract the carrier frequency from the power signals 340 and to derive a reference clock 348 from this frequency information extracted from the power signals 340. The reference clock 348 is then used by the short-range radio transceiver 320 to derive a carrier frequency of the transmitter block(s) 356 or as the local oscillator of the receiver block(s) 354.

As noted above, FIG. 3 illustrates an embodiment in which the reference clock 348 is derived from the carrier frequency of a continuous power signal transmitted on a closely-coupled link 331. It is to be appreciated that this specific implementation in which the closely-coupled link 331 carriers a continuous power signal is illustrative and that the techniques may be implemented with other type of signals transmitted using a predetermined carrier frequency. For example, in an alternative embodiment, both power and data may be modulated with a predetermined carrier frequency on a closely-coupled link. In a manner similar to that described in FIGS. 3 and 4, the carrier frequency could be extracted and used to generate the reference clock for a short-range radio transceiver.

Figure 5:
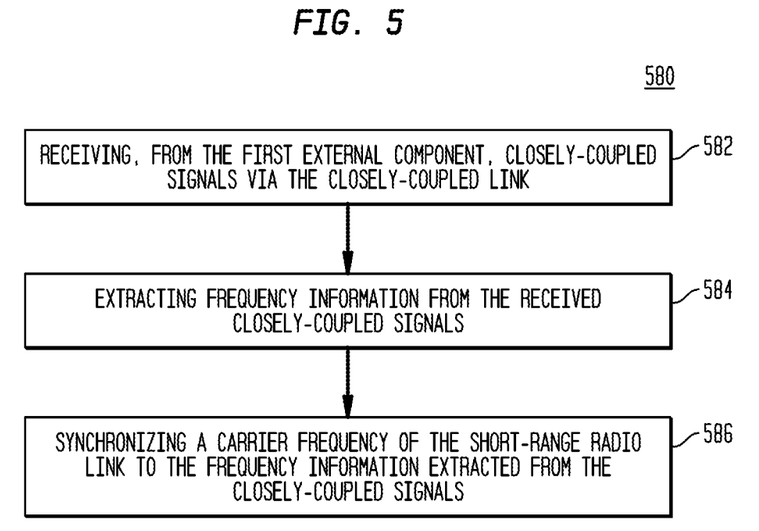
FIG. 5 is a flowchart of a method, in accordance with certain embodiments presented herein.

FIG. 5 is a flowchart of a method 580 in accordance with embodiments presented herein. Method 580 is performed at an implantable component in communication with a first external component via a closely-coupled link and in communication with a second external component via short-range radio link. Method 580 begins at 582 where the implantable component receives, from the first external component, closely-coupled signals via the closely-coupled link. At 584, the implantable component extracts frequency information from the received closely-coupled signals. At 586, a carrier frequency of the short-range radio link is synchronized to the frequency information extracted from the closely-coupled signals.

It is to be appreciated that the above described embodiments are not mutually exclusive and that the various embodiments can be combined in various manners and arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method performed at an implantable component in communication with a first external component via a link and in communication with a second external component via short-range radio link, the method comprising:
   receiving, from the first external component, signals via the link;
   extracting, with a reference clock extractor circuit, frequency information from the signals; and
   synchronizing a carrier frequency of the short-range radio link to the frequency information extracted from the signals.

2. The method of claim 1, wherein the signals are power signals transmitted in a series of pulse bursts, and wherein extracting frequency information from the signals comprises:
   extracting a pulse burst rate from the signals.

3. The method of claim 1, wherein the signals are one or more of power or data signals modulated at a particular carrier frequency, and wherein extracting frequency information from the signals comprises:
   extracting the particular carrier frequency from the signals.

4. The method of claim 1, wherein synchronizing a carrier frequency of the short-range radio link to the frequency information extracted from the signals comprises:
   deriving a transceiver reference clock in the implantable component from the frequency information extracted from the signals;
   generating, with one or more implantable frequency sources in the implantable component, one or more frequency signals based on the transceiver reference clock; and
   using the one or more frequency signals to at least one of transmit or receive data signals via the short-range radio link.

5. The method of claim 4, wherein using the one or more frequency signals to at least one of transmit or receive signals via the short-range radio link, comprises:
   using at least one of the one or more frequency signals as a carrier frequency for use in transmitting modulated data signals via the short-range radio link.

6. The method of claim 4, wherein using the one or more frequency signals to at least one of transmit or receive signals via the short-range radio link, comprises:
   using at least one of the one or more frequency signals as a mixing frequency for use in extracting data from modulated data signals received via the short-range radio link.

7. The method of claim 4, wherein generating, with one or more implantable frequency sources in the implantable component, one or more frequency signals based on the transceiver reference clock, comprises:
   providing the transceiver reference clock to at least one of a phase locked loop (PLL) system or a delay locked loop (DLL) system of the implantable component; and
   generating the one or more frequency signals with the at least one of the PLL or DLL system.

8. The method of claim 7, further comprising:
   converting the one or more frequency signals generated by the at least one of the PLL system or the DLL system before using the one or more frequency signals to at least one of transmit or receive data signals via the short-range radio link.

9. The method of claim 1, wherein the short-range radio link is a magnetic-induction (MI) link.

10. The method of claim 1, wherein the reference clock extractor circuit includes a multiplier-divider (M:N) logic circuit configured to generate a reference clock, and wherein the multiplier-divider (M:N) logic circuit is locked to the frequency information extracted from the signals received via the link.

11. An implantable component of an implantable medical device system, comprising:
   a first implantable coil coupled to a first external component via a link and configured to receive signals;
   a reference clock extractor circuit configured to extract frequency information from the signals received via the first implantable coil and to generate a reference clock based on the frequency information extracted from the signals; and
   a short-range radio transceiver configured to use the reference clock to at least one of transmit data signals to, or receive data signals from, a second external device via a short-range radio link,
   wherein a carrier frequency of the short-range radio link is synchronized to the frequency information extracted from the signals.

12. The implantable component of claim 11, wherein the signals are power signals transmitted in a series of pulse bursts, and wherein the reference clock extractor circuit is configured to extract a pulse burst rate from the signals for use in generating the reference clock.

13. The implantable component of claim 11, wherein the signals are one or more of power or data signals modulated at a particular carrier frequency, and wherein the reference clock extractor circuit is configured to extract the particular carrier frequency from the signals for use in generating the reference clock.

14. The implantable component of claim 11, wherein the reference clock extractor circuit includes a multiplier-divider (M:N) logic circuit configured to generate the reference clock, and wherein the multiplier-divider (M:N) logic circuit is locked to the frequency information extracted from the signals.

15. The implantable component of claim 10, wherein the short-range radio transceiver comprises one or more implantable frequency sources configured to generate one or more frequency signals based on the reference clock,
   wherein the short-range radio transceiver is configured to use the one or more frequency signals to at least one of transmit data signals to, or receive data signals from, the second external device via the short-range radio link.

16. The implantable component of claim 15, wherein to use the one or more frequency signals to at least one of transmit data signals to, or receive data signals from, the second external device via the short-range radio link, the short-range radio transceiver is configured to use at least one of the one or more frequency signals as a carrier frequency for use in transmitting modulated data signals via the short-range radio link.

17. The implantable component of claim 15, wherein to use the one or more frequency signals to at least one of transmit data signals to, or receive data signals from, the second external device via the short-range radio link, the short-range radio transceiver is configured to use at least one of the one or more frequency signals as a mixing frequency for use in extracting data from modulated data signals received via the short-range radio link.

18. The implantable component of claim 15, wherein the one or more implantable frequency sources comprise at least one of a phase locked loop (PLL) system or a delay locked loop (DLL) system.

19. The implantable component of claim 18, wherein the short-range radio transceiver comprises a converting block configured to convert the one or more frequency signals generated by the at least one of the PLL system or the DLL system before using the one or more frequency signals to at least one of transmit data signals to, or receive data signals from, the second external device via the short-range radio link.

20. The implantable component of claim 11, wherein the short-range radio transceiver is a magnetic-induction (MI) radio coupled to a magnetic induction coil.

\* \* \* \* \*